(12) United States Patent
Kwatra et al.

(10) Patent No.: US 11,363,953 B2
(45) Date of Patent: Jun. 21, 2022

(54) METHODS AND SYSTEMS FOR MANAGING MEDICAL ANOMALIES

(71) Applicant: INTERNATIONAL BUSINESS MACHINES CORPORATION, Armonk, NY (US)

(72) Inventors: Shikhar Kwatra, Morrisville, NC (US); Moitreyee Mukherjee-Roy, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 145 days.

(21) Appl. No.: 16/130,350

(22) Filed: Sep. 13, 2018

(65) Prior Publication Data

US 2020/0085300 A1    Mar. 19, 2020

(51) Int. Cl.
| | |
|---|---|
| A61B 5/00 | (2006.01) |
| G16H 10/60 | (2018.01) |
| G16H 15/00 | (2018.01) |
| G16H 80/00 | (2018.01) |
| A63B 24/00 | (2006.01) |

(Continued)

(52) U.S. Cl.
CPC ........ *A61B 5/0022* (2013.01); *A63B 24/0075* (2013.01); *G06N 3/02* (2013.01); *G16H 10/60* (2018.01); *G16H 15/00* (2018.01); *G16H 20/00* (2018.01); *G16H 80/00* (2018.01); *A63B 2024/0065* (2013.01)

(58) Field of Classification Search
CPC ... G06F 1/00–2221/2153; G16H 10/00–80/00; A61B 5/0002–5/7495; G06N 3/00–99/007
See application file for complete search history.

(56) References Cited

U.S. PATENT DOCUMENTS 5,362,069 A * 11/1994 Hall-Tipping ........ A63F 13/245
463/7
6,368,284 B1 * 4/2002 Bardy ................ A61N 1/36507
600/508

(Continued)

FOREIGN PATENT DOCUMENTS

| CN | 104462781 A * 3/2015 ............. G16Z 99/00 |
| CN | 107220524 A * 9/2017 |

(Continued)

OTHER PUBLICATIONS

Hunt et al., "Comparison of linear and nonlinear feedback control of heart rate fortreadmill running," Systems Science & Control Engineering, 4:1, 87-98. (Year: 2016).*

(Continued)

*Primary Examiner* — Jason B Dunham
*Assistant Examiner* — Jonathon A. Szumny
(74) *Attorney, Agent, or Firm* — Griffiths & Seaton PLLC

(57) ABSTRACT

Embodiments for managing medical anomalies by one or more processors are described. Medical data associated with an individual is received. The medical data is detected by a first computing device. The first computing device includes a mobile electronic device. The received medical data is compared to stored medical data associated with the individual. Based on the comparison of the received data to the stored data, a control signal for a second computing device is caused to be generated.

18 Claims, 8 Drawing Sheets

(51) Int. Cl.
*G16H 20/00* (2018.01)
*G06N 3/02* (2006.01)

(56) References Cited

U.S. PATENT DOCUMENTS

| | | | | |
|---|---|---|---|---|
| 6,702,719 | B1* | 3/2004 | Brown | G16H 10/60 |
| | | | | 482/8 |
| 2007/0033069 | A1* | 2/2007 | Rao | G16H 40/40 |
| | | | | 705/2 |
| 2012/0143019 | A1* | 6/2012 | Russell | A61B 5/6823 |
| | | | | 600/301 |
| 2013/0210579 | A1* | 8/2013 | Schieffer | G06F 19/3481 |
| | | | | 482/8 |
| 2014/0226529 | A1* | 8/2014 | Harris | H04W 8/005 |
| | | | | 370/255 |
| 2015/0351700 | A1* | 12/2015 | Franceschetti | A61B 5/01 |
| | | | | 600/484 |
| 2016/0321125 | A1* | 11/2016 | Kang | G06F 11/0706 |
| 2017/0031334 | A1 | 2/2017 | Medelius | |
| 2017/0142656 | A1* | 5/2017 | Hong | H04W 52/0229 |
| 2017/0144025 | A1* | 5/2017 | Abbondanza | G16H 20/30 |
| 2017/0149580 | A1 | 5/2017 | Bazar et al. | |
| 2017/0249713 | A1* | 8/2017 | Serbinis | G06Q 50/22 |
| 2017/0280495 | A1* | 9/2017 | Zhang | H04W 76/19 |
| 2018/0028896 | A1* | 2/2018 | Ray | A63B 71/0622 |
| 2018/0032691 | A1* | 2/2018 | Zur | A61B 5/002 |
| 2019/0038217 | A1* | 2/2019 | Cho | G16H 20/60 |
| 2019/0046037 | A1* | 2/2019 | Ramesh | H04L 67/12 |
| 2019/0073183 | A1* | 3/2019 | Yoshii | G06F 3/167 |
| 2019/0107993 | A1* | 4/2019 | Shibuya | G06F 3/16 |
| 2019/0117127 | A1* | 4/2019 | Keen | G06F 9/542 |
| 2019/0121803 | A1* | 4/2019 | Bertagna De Marchi | |
| | | | | G16H 40/63 |
| 2019/0314681 | A1* | 10/2019 | Yang | G06K 9/6267 |
| 2021/0219023 | A1* | 7/2021 | Sheng | A61B 5/7425 |

FOREIGN PATENT DOCUMENTS

| | | | | |
|---|---|---|---|---|
| CN | 103514355 B | * | 3/2018 | |
| WO | WO-2016037290 A1 | * | 3/2016 | G16H 40/67 |
| WO | 2016142338 A1 | | 9/2016 | |

OTHER PUBLICATIONS

Abdelgawad et al., "IoT-Based Health Monitoring System for Active and Assisted Living," ICST Institute for Computer Science, Social Informatics and Telecommunications Engineering 2017 (11 pages).

* cited by examiner

METHODS AND SYSTEMS FOR MANAGING MEDICAL ANOMALIES

BACKGROUND OF THE INVENTION

Field of the Invention

The present invention relates in general to computing systems, and more particularly, to various embodiments for managing anomalous medical or health conditions.

Description of the Related Art

Millions of people suffer from medical or health conditions, such as diabetes, heart disease, high blood pressure, etc., which may result from a poor diet and/or lack of exercise. However, in some situations, serious medical/health episodes or anomalies, related to such health conditions or otherwise, may arise when the individuals are performing activities with devices such as exercise equipment (e.g., treadmills), computing systems (e.g., gaming, virtual reality (VR), etc.), and various types of "smart" (e.g., "internet of things" (IoT)) devices.

For example, an individual running on a treadmill may be in danger if their heart rate exceeds a particular threshold. In such a situation, the individual may not realize the danger and/or not be able to react in time to prevent any serious complications. While some modern devices, such as smart watches, may help provide the individual with information related to their current health status, current systems may not be able to adequately make suitable changes to the individual's activity and/or provide a sufficient notification of the danger.

SUMMARY OF THE INVENTION

Various embodiments for managing medical anomalies by one or more processors are described. In one embodiment, by way of example only, a method for managing medical anomalies, again by one or more processors, is provided. Medical data associated with an individual is received. The medical data is detected by a first computing device. The first computing device includes a mobile electronic device. The received medical data is compared to stored medical data associated with the individual. Based on the comparison of the received data to the stored data, a control signal for a second computing device is caused to be generated.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
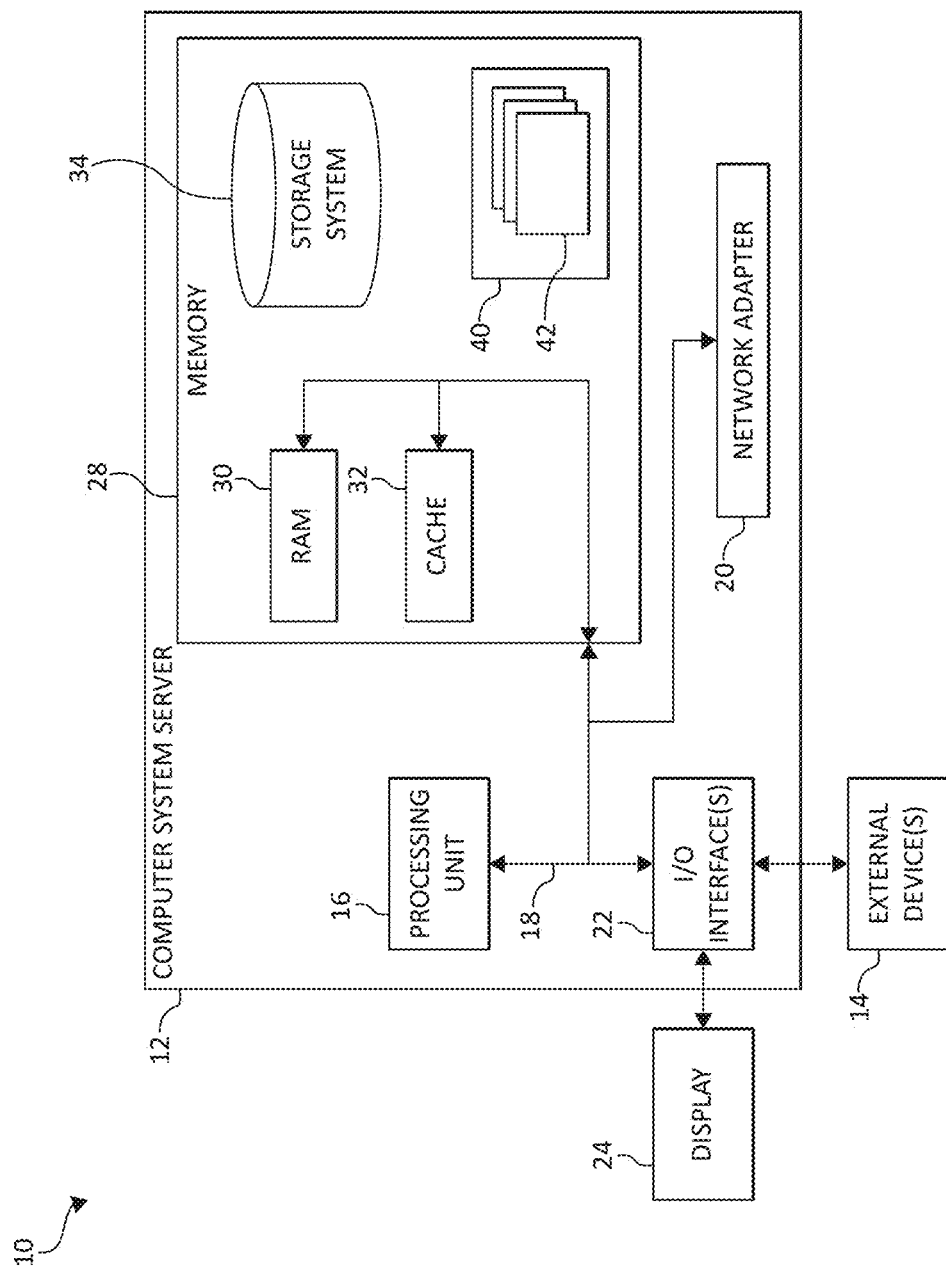
FIG. 1 is a block diagram depicting an exemplary computing node according to an embodiment of the present invention.

As discussed above, millions of people suffer from medical or health conditions, such as diabetes, heart disease, high blood pressure, etc. In some instances, the conditions result from poor diets and lack of exercise. In some situations, serious medical/health episodes, related to such health conditions or otherwise, may arise when the individuals are performing activities with devices such as exercise equipment (e.g., treadmills), computing systems (e.g., gaming, virtual reality (VR), etc.), and various types of "smart" (e.g., "internet of things" (IoT)) devices.

For example, an individual running on a treadmill may be in danger if their hear rate exceeds a particular threshold. In such a situation, the individual may not realize the danger and/or not be able to react in time to prevent any serious complications.

Although some modern devices, such as smart watches, are able to monitor the status of the individual with respect to various types of health or medical data, such as heart rate, blood pressure, oxygen levels, blood sugar levels, temperature, etc., current systems may not be able to adequately make suitable changes to the individuals activity and/or provide a sufficient notification of the danger.

With the increased presence of "smart" or "IoT" devices in peoples' daily lives, there is an untapped potential for integration of these devices to control the environment of users in such a way to preserve the health thereof and/or provide notifications to the users and/or others (e.g., family, contacts, doctors, emergency services, etc.) in the event that the users experience a serious medical condition (or health anomaly).

The methods and systems described herein may address some of these issues. They may be applicable to, for example, users who are not able to react adequately or in a timely manner to a communication from a health monitor. As a few specific examples, patients who were recently released from a hospital, but still need to be continuously monitored, and people whose cognitive abilities are declining, may be particularly able to benefit from the methods and systems described herein.

To address these needs, some embodiments described herein provide methods and systems that, for example, determine the best possible action to mitigate health risk given (or based on) a user's health pattern (e.g., history, medical records, etc.) and contextual situation, such as the user's location and the devices being utilized by and/or in proximity to the user. In some embodiments, at least one device (e.g., computing device) being utilized by and/or in proximity to the user is automatically controlled to mitigate the user's health risk and/or react to a health anomaly experienced by the user.

In some embodiments, a mobile electronic device near a user, such as a wearable technology device (e.g., a smart watch, head band, sociometric badge, camera clip, smart clothing, etc.) worn by the user, may act as an IoT device and communicate with other devices (e.g., other smart/IoT devices) being used by and/or in a proximity of the user. For example, the wearable device may detect that the user's heart rate exceeds a particular threshold (e.g., based on a profile or medical history of the user) while the user is on (or using) a piece of exercise equipment, such as a treadmill, step machine, or stationary bicycle. In such an instance, the data collected by the wearable device may be used to control the treadmill, such as by changing the speed (e.g., slowing down or stopping) the treadmill to reduce the heart rate of the user (e.g., at least to below the threshold). In some embodiments, such an action is taken automatically (e.g., without user/human intervention).

As such, in some embodiments, medical data is collected or recorded by a first device (e.g., a mobile electronic device) and evaluated and/or compared to other medical data (e.g., stored on a database). Based on the evaluation/comparison, a signal may be sent to a second device (e.g., a piece of exercise equipment), causing the operational state of the second device to change.

In some embodiments, in a situation such as described above, the wearable device may communicate with other devices to cause a notification or indication of the health condition to be generated. For example, computing devices such as mobile phones, laptops, tablet devices, etc. may be used to send a communication, such as a text message or email, to another individual or group of individuals, such as the user's family or contacts, doctor, or emergency services (e.g., to call an ambulance/medical personnel). The computing (or IoT) devices near the user may (also) be used to generate an aural and/or visual notification to alert the user of the potential health danger. For example, a speaker (e.g., on a laptop, on tablet, on a desktop PC, in earphones, or associated with another suitable device) may be used to generate an aural (or audible) alert, such as a voice prompt indicating the danger and/or instructing the user to change the speed of (or stop) the treadmill.

As such, in some embodiments, medical data is collected or recorded by a first device (e.g., a mobile electronic device) and evaluated and/or compared to other medical data (e.g., stored on a database). Based on the evaluation/comparison, a signal may be sent to a second device (e.g., another computing device in a proximity of the user), causing the second device to generate a notification of the health condition of the user.

In some embodiments, an analysis operation (e.g., a cognitive analysis) may be used to determine whether or not the current (or received) medical data associated with the user is indicative of a health anomaly or health-related risk. In some embodiments, the analysis operation includes generating a cognitive profile (e.g., a health profile or health anomaly or health-related risk profile) for the user(s) based on, for example, data sources associated with the user(s). Data sources that be use used to generate a cognitive profile for the user(s) may include any appropriate data sources associated with the user that are accessible by the system (perhaps with the permission or authorization of the user). Examples of such data sources include, but are not limited to a medical history or the medical records of the user(s), previous user activity (e.g., medical data at previous times/ during activities, location, proximity to/use of various devices, type of activities, etc.), communications (e.g., phone calls, video calls, text messaging, emails, in person/ face-to-face conversations, etc.), a profile of (or basic information about) the user (e.g., job title, place of work, length of time at current position, family role, etc.), a schedule or calendar (i.e., the items listed thereon, time frames, etc.), projects (e.g., past, current, or future work-related projects), location (e.g., previous and/or current location and/or location relative to other users), social media activity (e.g., posts, reactions, comments, groups, etc.), browsing history (e.g., web pages visited), and online purchases.

As such, in some embodiments, the methods and/or systems described herein may utilize a "cognitive analysis," "cognitive system," "machine learning," "cognitive modeling," "predictive analytics," and/or "data analytics," as is commonly understood by one skilled in the art. Generally, these processes may include, for example, receiving and/or retrieving multiple sets of inputs, and the associated outputs, of one or more systems and processing the data (e.g., using a computing system and/or processor) to generate or extract models, rules, etc. that correspond to, govern, and/or estimate the operation of the system(s), or with respect to the embodiments described herein, the management of medical anomalies as described herein. Utilizing the models, the performance (or operation) of the system (e.g., utilizing/ based on new inputs) may be predicted and/or the performance of the system may be optimized by investigating how changes in the input(s) effect the output(s).

It should be understood that as used herein, the term "computing node" (or simply "node") may refer to a computing device, such as a mobile electronic device or a desktop computer, and/or an application, such an email application, social media application, a web browser, etc. In other words, as used herein, examples of computing nodes include, for example, computing devices such as mobile phones, tablet devices, desktop computers, or workstations that are owned and/or otherwise associated with individuals (or users), and/or various applications that are utilized by the individuals on such computing devices.

In particular, in some embodiments, a method for managing medical anomalies by one or more processors is provided. Medical data associated with an individual is received. The medical data is detected by a first computing device. The first computing device includes a mobile electronic device. The received medical data is compared to stored medical data associated with the individual. Based on the comparison of the received data to the stored data, a control signal for a second computing device is caused to be generated.

The first computing device may include a wearable technology device. The comparing of the received medical data to the stored medical data may be performed utilizing an analysis operation (e.g., a cognitive analysis).

The second computing device may include exercise equipment. The control signal may be configured to change an operational state of the exercise equipment from a first setting to a second setting. The first and second settings may be associated with at least one of a speed of the exercise equipment and a resistance of the exercise equipment.

The control signal may be configured to cause the second computing device to generate a notification. The notification may include an electronic communication sent to a third computing device associated with a second individual. The notification may include at least one of a visual indication and an aural indication rendered in a proximity of the individual.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment, such as cellular networks, now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 (and/or one or more processors described herein) is capable of being implemented and/or performing (or causing or enabling) any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

In the context of the present invention, and as one of skill in the art will appreciate, various components depicted in FIG. 1 may be located in, for example, personal computer systems, server computer systems, thin clients, thick clients, hand-held or laptop devices, multiprocessor systems, microprocessor-based systems, set top boxes, programmable consumer electronics, network PCs, mobile electronic devices, such as mobile (or cellular and/or smart) phones, personal data assistants (PDAs), tablets, wearable technology devices, laptops, handheld game consoles, portable media players, etc., as well as computing systems in vehicles, such as automobiles, aircraft, watercrafts, and exercise equipment, such as treadmills, step machines, stationary bicycles, etc. However, in some embodiments, some of the components depicted in FIG. 1 may be located in a computing device in, for example, a satellite, such as a Global Position System (GPS) satellite. For example, some of the processing and data storage capabilities associated with mechanisms of the illustrated embodiments may take place locally via local processing components, while the same components are connected via a network to remotely located, distributed computing data processing and storage components to accomplish various purposes of the present invention. Again, as will be appreciated by one of ordinary skill in the art, the present illustration is intended to convey only a subset of what may be an entire connected network of distributed computing components that accomplish various inventive aspects collectively.

Figure 2:
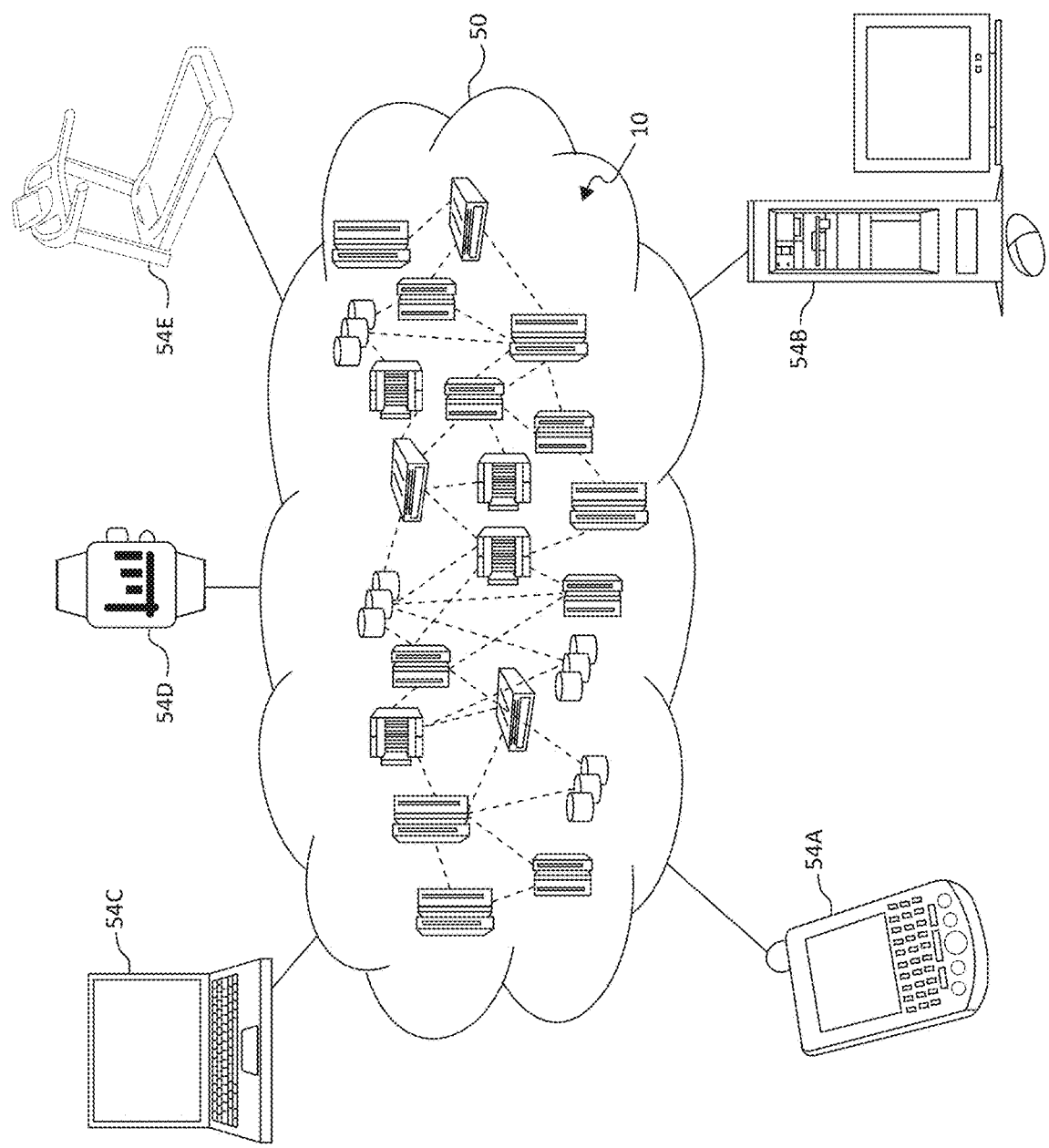
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, cellular (or mobile) telephone or PDA 54A, desktop computer 54B, laptop computer 54C, wearable technology device (e.g., smart watch) 54D, and exercise equipment (e.g., a smart/IoT treadmill) computing system 54E, may communicate.

Still referring to FIG. 2, nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-E shown in FIG. 2 are intended to be illustrative only and that computing nodes 10 and cloud computing environment 50 can communicate with any type of computerized device over any type of network and/or network addressable connection (e.g., using a web browser).

Figure 3:
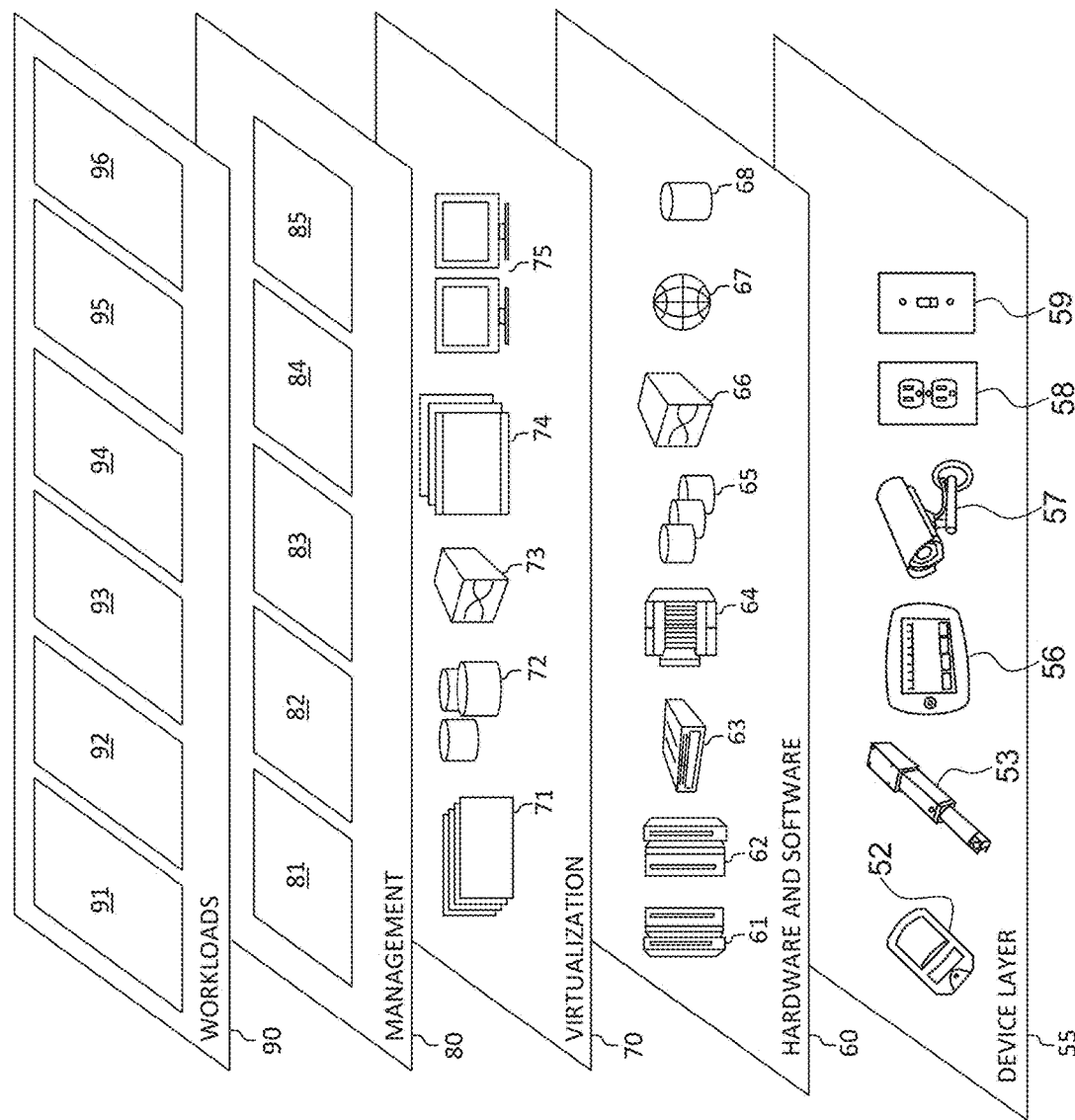
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to, wearable technology devices, pieces of exercising equipment, various additional sensor devices, networking devices, electronics devices (such as a remote control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for managing medical anomalies as described herein. One of ordinary skill in the art will appreciate that the workloads and functions 96 may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, in some embodiments, methods and systems are provided that, for example, monitor and/or collect medical data associated with a user (or individual) and determine the best possible action to mitigate health risk given (or based on) a user's health pattern (e.g., history, medical records, etc.) and contextual situation, such as the user's location and the devices being utilized by and/or in proximity to the user. In some embodiments, at least one device (e.g., computing device) being utilized by and/or in proximity to the user is automatically controlled to mitigate the user's health risk and/or react to a health anomaly experienced by the user.

In some embodiments, a mobile electronic device near a user, such as a wearable technology device (e.g., a smart watch) worn by the user, may act as an IoT device and communicate with other devices (e.g., other smart/IoT devices) being used by and/or in a proximity of the user. For example, the wearable device may detect that the user's heart rate exceeds a particular threshold (e.g., based on a profile or medical history of the user) while the user is on (or using) a piece of exercise equipment, such as a treadmill. In such an instance, the data collected by the wearable device may be used to control the treadmill, such as by changing the speed (e.g., slowing down or stopping) the treadmill to reduce the heart rate of the user (e.g., at least to below the threshold). In some embodiments, such an action is taken automatically (e.g., without user/human intervention).

In some embodiments, in a situation such as described above, the wearable device may communicate with other devices to cause a notification or indication of the health condition to be generated. For example, computing devices such as mobile phones, laptops, tablet devices, etc. may be used to send a communication, such as a text message or email, or make a phone call, to another individual or group of individuals, such as the user's family or contacts, doctor, or emergency services (e.g., to call an ambulance/medical personnel). The computing devices (or IoT) devices near the user may (also) be used to generate an aural and/or visual notification to alert the user of the potential health danger. For example, a speaker (e.g., on a laptop, on tablet, on a desktop PC, in earphones, or associated with another suitable device) may be used to generate an aural (or audible) alert, such as a voice prompt indicating the danger and/or instructing the user to change the speed of (or stop) the treadmill.

In some embodiments, the user has a first computing device, such as a mobile electronic device, within a proximity of their body. For example, the first computing device may be a mobile phone or wearable technology device, such as a smart watch or other device, strapped to their arm, which is capable of monitoring user activity and/or collecting medical data. Although embodiments described herein may repeatedly refer to cardiac data, such as heart rate, it should be understood that the methods and systems described herein may be applied to other types of medical data (and/or devices capable of monitoring other types of medical data), such as blood pressure, blood sugar levels, oxygen levels, temperature, or any other physiological data/metrics that may be used to determine the health status of an organism (e.g., person, animal, etc.).

The user's medical data may be collected (or detected) by the first device and stored on a local memory (or cache) thereof. For example, the collected medical data may include heart rate, heart beat patters, blood pressure (e.g., systolic and/or diastolic), etc.

In some embodiments, the user's medical data is transferred (e.g., via wireless communication) from the local memory to a database or intelligent medical/health condition management component (e.g., remote, on the cloud, etc.). In some embodiments, the medical data is constantly collected and/or stored and transferred to the database such that the "current" status of the user is constantly updated. In some embodiments, the medical data is transferred to the database when an anomaly in the medical data is detected (or determined) by the first device (e.g., if the first device detects a heart rate that it determines to be dangerously high and/or above a first threshold).

The medical data, along with data associated with the activity, location, etc. of the user, may be accessed by medical personnel (e.g., a doctor) from the database who may utilize such to monitor the user. The data may also be utilized by the system (perhaps with user and/or medical personnel feedback) to generate a cognitive (or medical) profile for the user (e.g., via a cognitive analysis), which may include thresholds (e.g., upper and lower thresholds, different levels regarding severity, etc.) for various types of medical data (e.g., heart rate, blood pressure, etc.) associated with the user. The thresholds may be utilized by the system (and/or any devices associated with the user) to initiate the generation of control signals for (second) devices, as described herein.

In some embodiments, if the medical data collected by the first device indicates that a physiological condition (e.g., the user's heart rate) exceeds a particular threshold (e.g., a second threshold) and/or exhibits some other type of abnormal behavior (e.g., a quick, significant change), a notification may be generated by a second computing device (e.g., the user's mobile phone). For example, a notification (e.g., an electronic communication or message) may be sent to other computing devices, such as those owned by, registered to, etc. contacts of the user, such as family member and/or friends (e.g., predetermined/set by the user) or the user's doctor. The notification may indicate that the contacts may want to check on the user and/or schedule a meeting with the user (e.g., in the case of a doctor).

In some embodiments, perhaps depending on the severity of the health condition indicated by the medical data collected by the first device (e.g., a third threshold is exceeded), the generating of the notification may include contacting (e.g., sending an electronic communication or via phone call) medical personnel, such as a medical personnel and/or emergency services. For example, the user's mobile phone may automatically call emergency services (e.g., "911") and provide an automated voice prompt, alerting the receiver(s) of the call of the health condition of the user.

In some embodiments, perhaps depending on the severity of the health condition, the generating of the notification may include causing an aural and/or visual notification to be rendered by a (second) computing device in the proximity of the user to alert the user of the health risk/condition. For example, a computing device, such as a mobile phone, laptop, tablet device, or desktop computer that is equipped with a speaker, that is in the same room as the user or within a predetermined distance may be controlled to generate an audible alert and/or a visual alert (e.g., a flashing display device, a text-based message on the display device, etc.). It should be understood that any device (e.g., IoT device) that is in operable communication with the system may be utilized in this regard. For example, an audile alert may also be generated by an IoT doorbell or an appliance that is equipped with a speaker (e.g., a microwave oven, washer/dryer, refrigerator, etc.). Similarly, other IoT devices may be utilized to generate visual notifications (e.g., dimming and/or flashing lights).

In some embodiments, if the medical data collected by the first device indicates that a physiological condition (e.g., the user's heart rate) exceeds a particular threshold (e.g., a second threshold) and/or exhibits some other type of abnormal behavior (e.g., a quick, significant change), a control signal for a second computing device that is being utilized by the user is generated. For example, if it is determined that the user is running on a treadmill (e.g., an IoT treadmill) when the health condition is detected, the control signal may change the operational state of the treadmill (e.g., reduce the speed or resistance/incline thereof) to ameliorate the health condition (e.g., to lower the heart rate of the user to below a particular threshold).

In some embodiments, during an initial or set up stage of operation, a Message Queuing Telemetry Transport (MQTT) (or similar protocol) or internet-based proximity search query is performed to identify devices near the user and/or the first computing device (e.g., a wearable technology device) to determined if the devices are paired (or in operable communication with each other). Once the devices are paired and a communication channel (e.g., duplex communication channel) has been established, the user's vital signs (or medical data) are calibrated in correlation with other sensory devices. For example, readings from accelerometer to determine the speed of the user while running on a treadmill may be calibrated with command instructions to the treadmill (e.g., regarding running/walking belt speed).

A feedback learning model (or intelligent medical/health condition management component) may, over time, learn the user's activities and/or and cognitive heuristics in conjunction with activities performed by the user (e.g., running on a treadmill, playing a game, experiencing a VR session, etc.), along with the user's vital signs (or typical vital signs) and devices used during the activities.

In some embodiments, after correlations are established, the pairing with various devices is performed automatically the next time the user is in a similar contextual situation (e.g., performing a similar activity) to monitor the user's medical data and cause suitable control signals for other devices to be generated (e.g., to change the operational state of the other devices, cause notifications to be generated, etc.) based on the learned behaviors/activities of the user and medical data associated with that behavior/those activities.

In some embodiments, at least for calibration and configuration, the system (for monitoring and reporting the user's proximal status information, includes a database, a communication interface, and a system manager. The database may store status information associated with a second device (e.g., a piece of exercise equipment) and the activity performed. The communication interface may be configured to allow communication (e.g., wireless communication) with devices located remotely from the first device (e.g., a wearable technology device). The system manager may receive messages transmitted from the first device and update the status information stored in the database based on the received message.

When a second device establishes communication with the communication interface, identification information may be automatically sent from the second device to the communication interface. The system manager may analyze the identification information and automatically retrieve status information from the database based on the identification information, proximal distance, and activity performed by the user (e.g., recorded during an initial machine learning/cognitive building/training phase). The system manager may then transmit, via the communication interface, the retrieved status information to the second device, allowing acknowledgement to morph the content or control functional parameter based on the properties of the second device.

For example, if the user is running on a treadmill at a relatively high speed, and the user's heart rate is detected as exceeding a specific threshold, the first device (e.g., a wearable device) may detect the anomaly and instructions (e.g., cloud-based instructions) may be sent to the treadmill to reduce the speed thereof (e.g., to reduce the user's heart rate to below the threshold).

Figure 4:
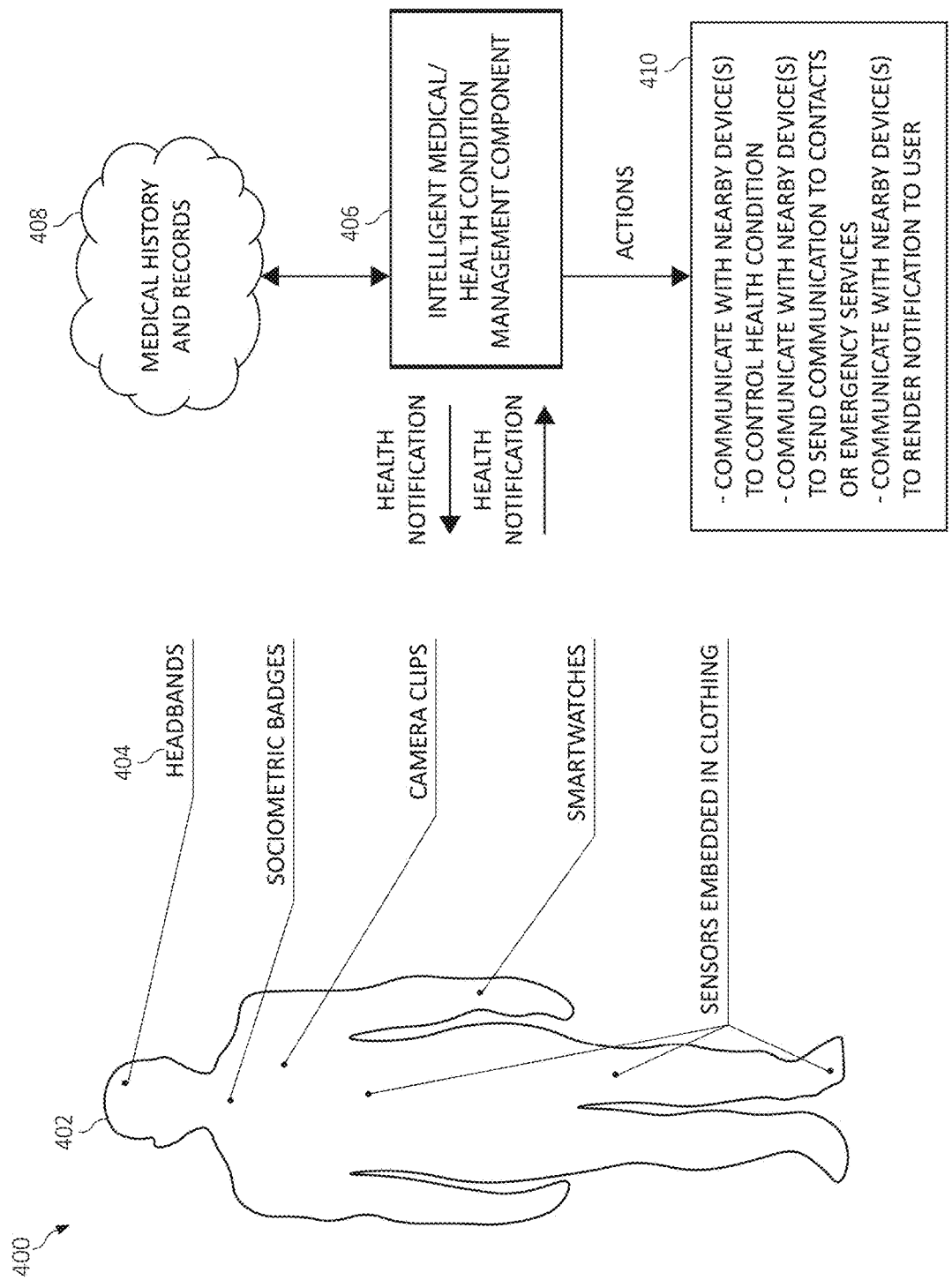
FIG. 4 is a block diagram of a computing environment according to an embodiment of the present invention.

FIG. 4 illustrates a computing environment (or system) 400 according to some embodiments of the present invention. The environment 400 includes a user 402 with at least one computing device (i.e., a first device) 404 in close proximity thereto, an intelligent medical/health condition management component (e.g., intelligent medical/health condition management component) 406, and a database 408.

In some embodiments, the first device 404 includes a wearable technology device (or multiple wearable technology devices), such a smart watches, headband, sociometric badge, camera clip, and smart clothing (e.g., having sensors embedded therein). Generally, the wearable technology device(s) 404 is configured to collect various type of data about the user 402 and/or the activity thereof, including medical data or vital signs, location, activity type/level, etc. Examples of data that may be collected or monitored by the wearable technology device(s) 404 include, but are not limited to, heart rate, heart function/beat patterns (e.g., via an electrocardiogram (ECG)), blood pressure, oxygen levels, blood sugar levels, temperature, brain activity (e.g., via an electroencephalogram (EEG)), and muscle/nerve health/activity (e.g., via an electromyography (EMG)), along with location, altitude, atmospheric conditions, etc.

The intelligent medical/health condition management component (e.g., "cognitive module" or system manager, control system, etc.) 406 may include any suitable computing system, such as those described above, and may be located remotely from the user 402 (e.g., in a different city, on the cloud, etc.), as may the database 408. The database 408 includes (or has stored thereon), for example, the medical history and/or medical records (and perhaps previous medical data associated with the user 402 collected from the wearable technology device).

As described above, data collected by the wearable technology device 404 is sent (e.g., via wireless communication) to the intelligent medical/health condition management component 406. The intelligent medical/health condition management component 406 may, for example, compare the received medical data to medical data for the user 402, a cognitive profile for the user 402, and/or thresholds for various types of medical data (e.g., determined via a cognitive analysis) to determine if the user 402 is experiencing a health anomaly (or the probability thereof), the severity of the anomaly, and/or a health risk associated with the user's current activity (e.g., based on the most recent medical data received from the wearable technology device 404 and the current activity of the user 402).

In some embodiments, when a health anomaly is detected or determined, the intelligent medical/health condition management component 406 takes one or more action 410. In some embodiments, the intelligent medical/health condition management component 406 generates a signal that may be used to control a second computing device (e.g., a piece of exercise equipment or another computing device), perhaps depending on the severity of the health anomaly. For example, if the user 402 is using a treadmill, and the user's heart rate is determined to exceed a predetermined threshold, a control signal for the treadmill may be generated and transmitted to the treadmill (e.g., via wireless communication), which may change the operational state of the treadmill by, for example, reducing the speed of the treadmill to control the health anomaly (or condition) (e.g., to reduce the heart rate of the user 402). As another example, the intelligent medical/health condition management component 406 may generate a control signal for another computing device (or IoT device), such as a mobile phone or desktop computer, causing a notification to be generated. The notification may include a message sent to another (third) computing device associated with another individual or group of individuals (e.g., family, friends, medical personnel, etc.) and/or an aural and/or visual notification generated in the proximity of the user 402 (e.g., via a speaker associated with a computing device near the user 402).

Figure 5:
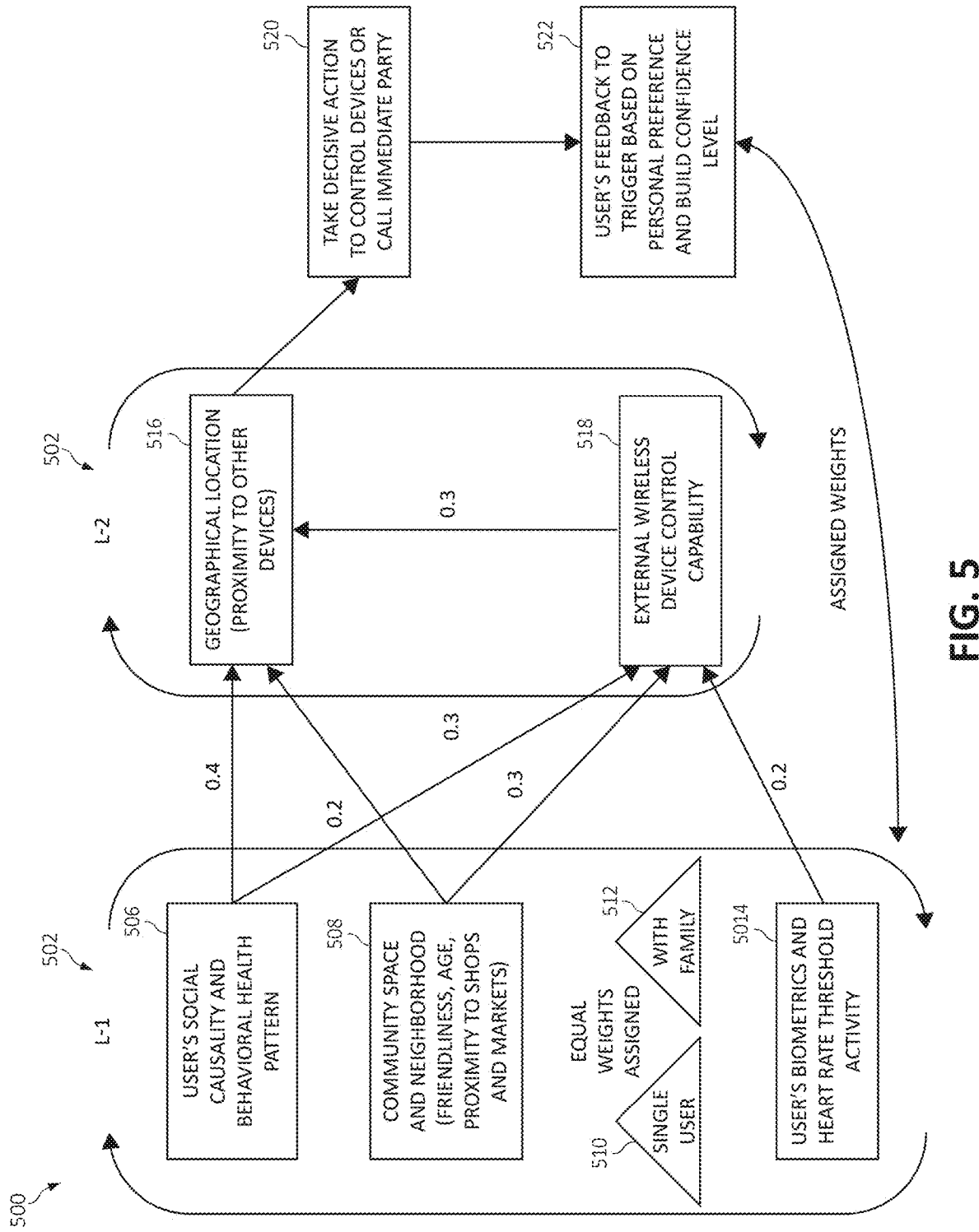
FIG. 5 is a diagram of a classification model according to an embodiment of the present invention.

FIG. 5 illustrates a multi-level neural network classification model (or deep learning cognitive mechanism with variable features) 500 according to some embodiments described herein. The model 500 may, for example, proactively obtain user feedback and medical data from the user(s) to determine when to take action with respect to the medical/health condition of the user(s). The model 500 includes a first layer (L-1) 502 and a second layer (L-2) 504.

The first layer 502 includes (and/or utilizes) the user's social causality and behavior health pattern (e.g., activity types, social media activity, etc.) 506, details related to the user's community space and neighborhood 508 (e.g., friendliness, average age, proximity to shops/markets, etc. and based on information related to the user, such as whether or not the user is single 510 or has a family 512), and the user's biometrics (e.g., medical data) and thresholds/threshold activities 514. The second layer 504 includes (and/or utilizes) the user's (and/or user's device) geographical location (and/or proximity to other devices) 516 and the control capabilities of external wireless devices (e.g., second computing device) 518.

From the geographical location information 516 (e.g., and based on the other factors shown), an action 520 (e.g., control a second device, call another party, etc.) is taken (i.e., within a third layer of the model 500), and user feedback 522 is received. The user feedback 522 may be used to train the first layer 502. The various factors utilized by the model 500 may be assigned configurable weights to tune the determination of whether or not to take any action with respect to the health condition of the user and/or which action to take.

Figure 6:
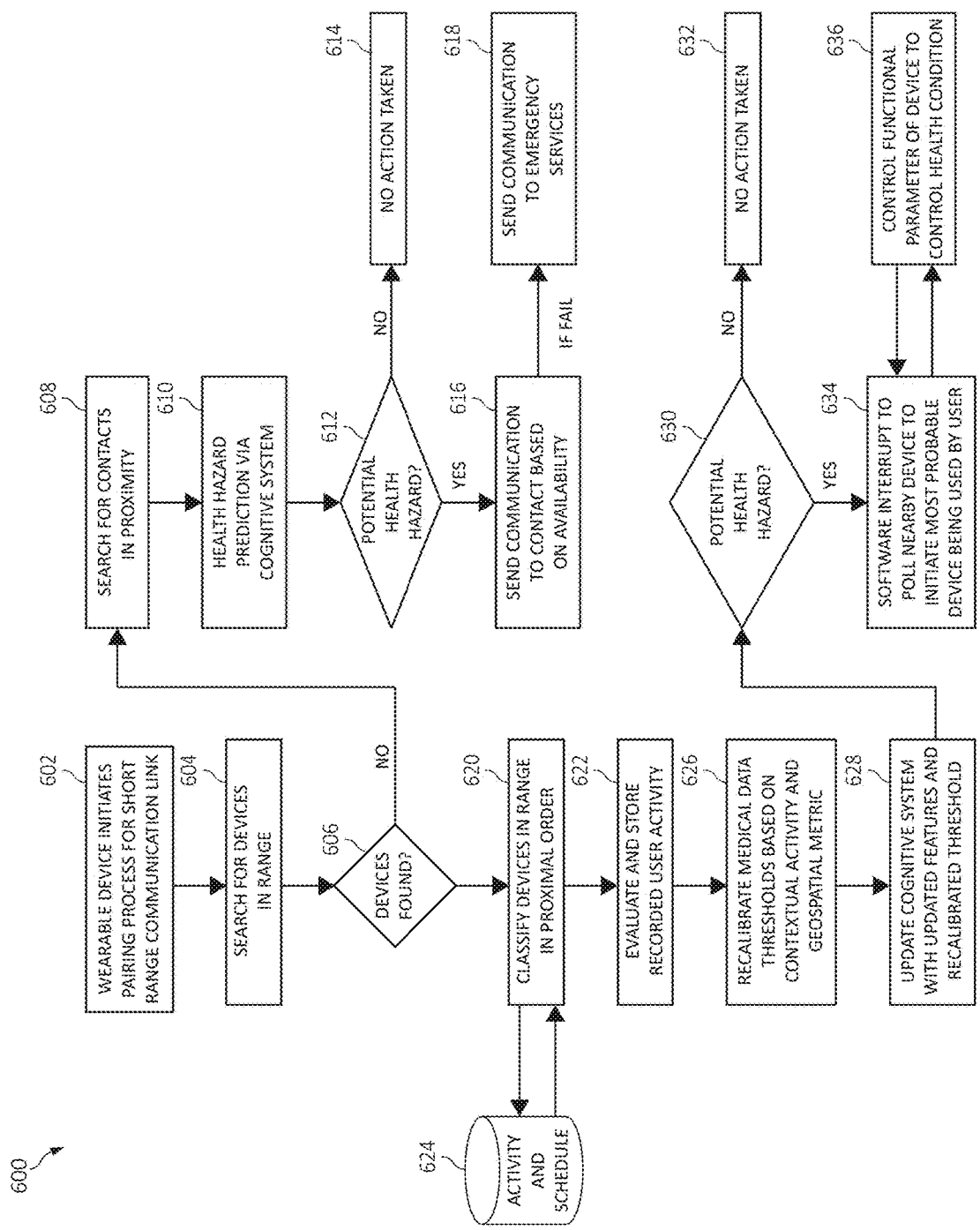
FIG. 6 is a flow chart/block diagram of exemplary method and/or system according to an embodiment of the present invention.

FIG. 6 illustrates a flowchart/block diagram of a method (and/or system) 600 according to some embodiments described herein. In particular, FIG. 6 may illustrate a method/system for connecting computing devices of interest and taking an action based on the detected medical data of a user. At block 602, a first device (e.g., a wearable device worn by the user) initiates a pairing process for a short range communication link with other suitable devices. At block 604, a search for other suitable devices (e.g., second computing devices that are being utilized by the user, such as exercise equipment of VR system) is performed.

At block 606, if no such devices are located (or perhaps even if such devices are located), the method proceeds to block 608, at which point a search is performed for contacts (e.g., family, friends, a doctor, etc.) within a proximity (e.g., within a predetermined distance, such as 10 miles) of the user (e.g., as listed in the user's mobile phone, social media profile, etc.). At block 610, health hazard (or anomaly or condition) prediction is performed (e.g., via a cognitive system) based on, for example, medical data collected by the wearable device. At block 612, if no potential health hazard is detected, no action is taken at block 614. If a potential health hazard is detected, a communication is sent to a contact (e.g., via a phone call, text message, etc.) by an appropriate device (e.g., the user's mobile phone, tablet, etc.) at block 616. If it is determined that the communication did not successfully alert the contact (e.g., the phone call was not answered), at block 618, a (second) communication is sent to another party, such as emergency services.

Returning to block 606, if such devices are located, the devices are classified in a proximal order (e.g., in order of which devices are closest/most accessible to the user) at block 620. At block 622, user activity and/or medical data collected by the wearable device is evaluated and stored (e.g., on database 624, perhaps along with a schedule of the user). At block 626, thresholds associated with the received medical data are calibrated (or recalibrated) based on, for example, the contextual activity and/or geospatial metrics of the user. At block 628, the cognitive system is updated with new (or updated) features and the (re)calibrated thresholds. At block 630, if no potential health hazard is detected (or determined), no action is taken at block 632. If a potential health hazard is detected, at block 634, a software interrupt is performed to poll nearby devices to initiate the most probable device (e.g., exercise equipment, a VR system, etc.) being used by the user. At block 636, a signal is generated to control a functional parameter of the device to control (or ameliorate) the health condition (or hazard). The method/system 600 may loop back to block 634, for example, if no changes to the medical data are detected after the functional parameter is changed (e.g., the user's heart rate does not decrease after the treadmill is slowed down) to ensure the correct device is being controlled.

Figure 7:
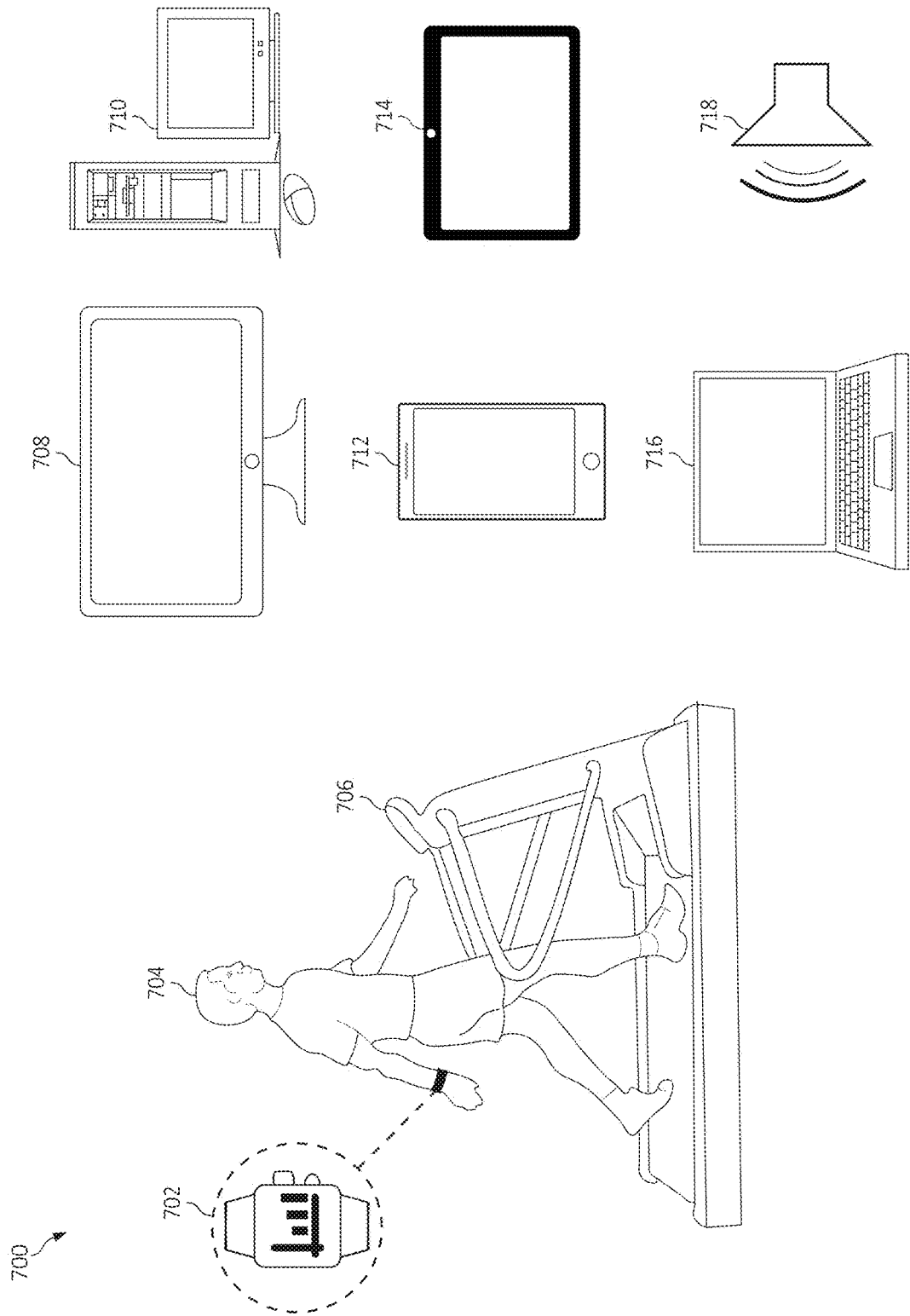
FIG. 7 is a plan view of a computing system according to an embodiment of the present invention.

FIG. 7 illustrates a system 700 according to some embodiments described herein. The system includes a first computing device in close proximity to a user 704. In the depicted embodiment, the first device is a smart watch 702 worn by the user 704, while the user 704 is using (e.g., walking on, running on, etc.) a treadmill (or smart/IoT treadmill) 706. The system 700 also includes various other (or second/secondary) computing devices that may be within a vicinity of the user 704 and/or the treadmill 706, such as a smart television 708, a desktop PC 710, a mobile phone 712, a tablet device 714, a laptop computer 716, and a speaker 718. The speaker 718 may be integrated into and/or in operable communication with any of devices 708-716 or another IoT device/system, such as a doorbell or appliance.

As described above, one or more of the devices 708-718 may be utilized to automatically generate a notification to the user 704 and/or other individuals (e.g., family, friends, emergency services, etc.) if medical data collected by the smart watch 702 is determined to indicate a potential health condition of the user 704. For example, the mobile phone 712 may be utilized to place an automated phone call to a family member or friend of the user or emergency services. The tablet 714 may be utilized to send an email to a contact of the user 704, such as a family member or doctor. Also, the devices 708-718 may be utilized to generate an aural and/or visual notification or indication for the user 704. For example, an audible alert may be rendered by the speaker 718 and/or the screen of the smart television 708 may repeatedly flash or display a message, alerting the user 704 of the health condition.

Figure 8:
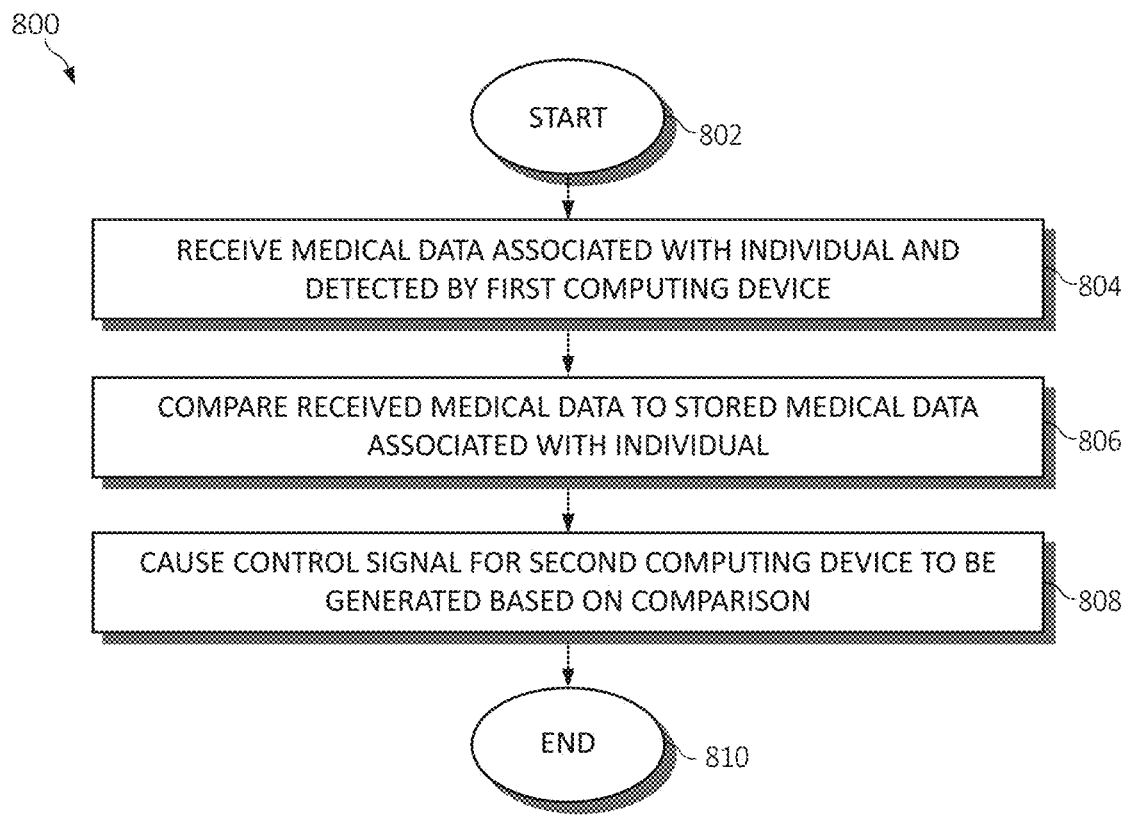
FIG. 8 is a flowchart diagram of an exemplary method for managing health anomalies according to an embodiment of the present invention.

Turning to FIG. 8, a flowchart diagram of an exemplary method 800 for managing medical anomalies, in accordance with various aspects of the present invention, is provided. Method 800 begins (step 602) with, for example, a first computing device that is capable of collecting medical data being utilized by an individual (or user) and/or the first computing device pairing with other computing devices in the vicinity of the individual.

Medical data associated with the individual is received (step 804). The medical data is detected by the first computing device. The first computing device may includes mobile electronic device, such as a wearable technology device (e.g., a smart watch).

The received medical data is compared to stored medical data associated with the individual (step 806). The comparing of the received medical data to the stored medical data may be performed utilizing a cognitive analysis. The stored medical data may be stored on a database that is remote from the individual (e.g., on the cloud).

Based on the comparison of the received data to the stored data (e.g., if a potential health condition is detected), a control signal for a second computing device is caused to be generated (step 808). The second computing device may include exercise equipment. The control signal may be configured to change an operational state of the exercise equipment from a first setting to a second setting. The first and second settings may be associated with at least one of a speed of the exercise equipment and a resistance of the exercise equipment. The control signal may be configured to cause the second computing device to generate a notification. The notification may include an electronic communication sent to a third computing device associated with a second individual. The notification may include at least one of a visual indication and an aural indication rendered in a proximity of the individual.

Method 800 ends (step 810) with, for example, the health condition being address by, for example, a notification being generated and provided to the appropriate individuals (e.g., the user, family/friends of the individual, medical personnel, etc.) and/or the operational state of a device being used by the individual being changed to ameliorate the health condition. In some embodiments, the individual (or another user) may provide feedback related to the accuracy or usefulness of the notifications and/or control of the secondary device, which may be utilized by the system to improve performance over time.

As such, in some embodiments, methods and systems for utilizing various computing devices to manage health (or medical) anomalies are provided. Medical (or health) data may be collected by a first device. The medical data may be evaluated and/or compared to a model of positive/negative medical/health events. If a health anomaly is detected, a second device may be communicated with. In some embodiments, an operational state of the second device is changed to, for example, ameliorate the health anomaly.

In some embodiments, IoT based machine-to-machine (M2M) communication is utilized to take prompt action when health anomalies are detected. Health anomalies may be predicted or detected based on medical data collected by a mobile electronic device, such as a wearable technology device. Other devices may be connected with based on the monitoring of the user's activity while engaging the respective objects/devices based on geo-spatial metrics and haptic feedback.

A MQTT protocol or internet based proximity search query may be initially performed to locate nearby devices in order to received acknowledgement if the devices are paired. The wearable device may have the capability to coordinate simultaneously with all linked devices, including VR headsets, speakers (in the vicinity), or the user's plugged earphones. If, for example, the user's heart rate is detected as exceeding a specific threshold, the wearable device may communicate with the other devices to take an action to slow the user's heart rate the pace, perhaps using an enabled voice recognition based system (e.g., via voice/speech prompts or other type of aural indication).

In some embodiments, the communication with other devices is performed via wireless communication (e.g., using piconets) and times for different types of activities for the user are stored in a database (e.g., on the cloud) along with respective vital signs to develop a rigidity factor for reinforcement. A deep learning mechanism may be utilized in conjunction with an analysis engine in order to keep maintain the system's capability of integrating the user's real0time health and activity pattern to identify future health hazards and control nearby devices to take ameliorative steps.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method, by one or more processors, for managing medical anomalies comprising:
   receiving medical data associated with an individual, wherein the medical data is detected by a first computing device, the first computing device including a mobile electronic device;
   transmitting the received medical data from the first computing device to a database remotely located from the first computing device, the database maintained by a cloud-based service;
   comparing, by the cloud-based service, the received medical data by the first computing device to stored medical data associated with the individual maintained in the database, wherein the stored medical data includes medical information obtained from a plurality of sources;
   based on the comparison of the received data to the stored data, determining, by the cloud-based service, that a medical anomaly is occurring that presents a health risk to the individual, wherein the comparison includes comparing at least some of the received medical data to a predetermined threshold;
   responsive to determining the medical anomaly is occurring based on the received medical data surpassing the predetermined threshold, issuing instructions by the cloud-based service instructing the first computing device to generate a control signal to command a second computing device to perform an action to facilitate correction of the medical anomaly, wherein the second computing device is identified by performing a software interrupt to poll proximally located devices to the first computing device, classifying the proximally located devices in a proximal order, and selecting the second computing device as one of the proximally located devices classified in proximal order as a most probable device being used by the individual which is a factor in causing the medical anomaly;
   transmitting the control signal to the second computing device as a software interrupt, wherein the control signal further includes, when the comparison indicates the received medical data surpasses a second predetermined threshold above the predetermined threshold, configuring any capable computing device within a predefined proximity of the individual to generate a notification, and wherein the any capable computing device is any computing device in network communication, as discovered by the polling, with the first computing device capable of generating the notification notwithstanding whether the any capable computing device is specifically preconfigured to generate the notification;
   training a neural network with the received medical data, the stored medical data, and features associated with parameters of the second computing device with regard to the action performed responsive to the determination of the medical anomaly occurring to generate a cognitive model of the user; and
   during a second session, subsequent to the first session, in which the user interacts with the second computing device, using the cognitive model of the user to determine the control signal transmitted from the first computing device to the second computing device during the second session including determining whether to update the predetermined threshold used to determine the medical anomaly is occurring during the second session, wherein, when the predetermined threshold is updated, the control signal to command the second computing device to perform the action to facilitate correction of the medical anomaly is generated during the second session based on the updated predetermined threshold, and wherein information associated with the updated predetermined threshold is used as feedback in re-training the neural network such that the cognitive model is recursively updated.

2. The method of claim 1, wherein the first computing device includes a wearable technology device.

3. The method of claim 1, wherein the comparing of the received medical data to the stored medical data is performed utilizing an analysis operation.

4. The method of claim 1, wherein the second computing device includes exercise equipment, and wherein the control signal is further configured to change an operational state of the exercise equipment from a first setting to a second setting, the first and second settings being associated with at least one of a speed of the exercise equipment and a resistance of the exercise equipment.

5. The method of claim 1, wherein the notification further includes an electronic communication sent to a third computing device associated with a second individual.

6. The method of claim 1, wherein the notification includes at least one of a visual indication and an aural indication rendered by the any capable computing device in the predefined proximity of the individual.

7. A system for managing medical anomalies comprising:
   at least one processor that
      receives medical data associated with an individual, wherein the medical data is detected by a first computing device, the first computing device including a mobile electronic device;
      transmits the received medical data from the first device to a database remotely located from the first computing device, the database maintained by a cloud-based service;
      compares, by the cloud-based service, the received medical data by the first computing device to stored medical data associated with the individual maintained in the database, wherein the stored medical data includes medical information obtained from a plurality of sources;
      based on the comparison of the received data to the stored data, determines that a medical anomaly is occurring that presents a health risk to the individual, wherein the comparison includes comparing at least some of the received medical data to a predetermined threshold;

responsive to determining the medical anomaly is occurring based on the received medical data surpassing the predetermined threshold, issues instructions by the cloud-based service instructing the first computing device to generate a control signal to command a second computing device to perform an action to facilitate correction of the medical anomaly, wherein the second computing device is identified by performing a software interrupt to poll proximally located devices to the first computing device, classifying the proximally located devices in a proximal order, and selecting the second computing device as one of the proximally located devices classified in proximal order as a most probable device being used by the individual which is a factor in causing the medical anomaly;

transmits the control signal to the second computing device as a software interrupt, wherein the control signal further includes, when the comparison indicates the received medical data surpasses a second predetermined threshold above the predetermined threshold, configuring any capable computing device within a predefined proximity of the individual to generate a notification, and wherein the any capable computing device is any computing device in network communication, as discovered by the polling, with the first computing device capable of generating the notification notwithstanding whether the any capable computing device is specifically preconfigured to generate the notification;

trains a neural network with the received medical data, the stored medical data, and features associated with parameters of the second computing device with regard to the action performed responsive to the determination of the medical anomaly occurring to generate a cognitive model of the user; and during a second session, subsequent to the first session, in which the user interacts with the second computing device, uses the cognitive model of the user to determine the command instructions transmitted from the first computing device to the second computing device during the second session including determining whether to update the predetermined threshold used to determine the medical anomaly is occurring during the second session, wherein, when the predetermined threshold is updated, the control signal to command the second computing device to perform the action to facilitate correction of the medical anomaly is generated during the second session based on the updated predetermined threshold, and wherein information associated with the updated predetermined threshold is used as feedback in re-training the neural network such that the cognitive model is recursively updated.

8. The system of claim 7, wherein the first computing device includes a wearable technology device.

9. The system of claim 7, wherein the comparing of the received medical data to the stored medical data is performed utilizing an analysis operation.

10. The system of claim 7, wherein the second computing device includes exercise equipment, and wherein the control signal is further configured to change an operational state of the exercise equipment from a first setting to a second setting, the first and second settings being associated with at least one of a speed of the exercise equipment and a resistance of the exercise equipment.

11. The system of claim 7, wherein the notification further includes an electronic communication sent to a third computing device associated with a second individual.

12. The system of claim 7, wherein the notification includes at least one of a visual indication and an aural indication rendered by the any capable computing device in the predefined proximity of the individual.

13. A non-transitory computer-readable storage medium having computer-readable program code portions stored therein for managing medical anomalies by one or more processors, the computer-readable program code portions comprising:

an executable portion that receives medical data associated with an individual, wherein the medical data is detected by a first computing device, the first computing device including a mobile electronic device;

an executable portion that transmits the received medical data from the first device to a database remotely located from the first computing device, the database maintained by a cloud-based service;

an executable portion that compares, by the cloud-based service, the received medical data by the first computing device to stored medical data associated with the individual maintained in the database, wherein the stored medical data includes medical information obtained from a plurality of sources;

an executable portion that, based on the comparison of the received data to the stored data, determining that a medical anomaly is occurring that presents a health risk to the individual, wherein the comparison includes comparing at least some of the received medical data to a predetermined threshold;

an executable portion that, responsive to determining the medical anomaly is occurring based on the received medical data surpassing the predetermined threshold, issues instructions by the cloud-based service instructing the first computing device to generate a control signal to command a second computing device to perform an action to facilitate correction of the medical anomaly, wherein the second computing device is identified by performing a software interrupt to poll proximally located devices to the first computing device, classifying the proximally located devices in a proximal order, and selecting the second computing device as one of the proximally located devices classified in proximal order as a most probable device being used by the individual which is a factor in causing the medical anomaly;

an executable portion that transmits the control signal to the second computing device as a software interrupt, wherein the control signal further includes, when the comparison indicates the received medical data surpasses a second predetermined threshold above the predetermined threshold, configuring any capable computing device within a predefined proximity of the individual to generate a notification, and wherein the any capable computing device is any computing device in network communication, as discovered by the polling, with the first computing device capable of generating the notification notwithstanding whether the any capable computing device is specifically preconfigured to generate the notification;

an executable portion that trains a neural network with the received medical data, the stored medical data, and features associated with parameters of the second computing device with regard to the action performed responsive to the determination of the medical anomaly occurring to generate a cognitive model of the user; and an executable portion that, during a second session, subsequent to the first session, in which the user interacts with the second computing device, uses the cognitive model of the user to determine the command instructions transmitted from the first computing device to the second computing device during the second session including determining whether to update the predetermined threshold used to determine the medical anomaly is occurring during the second session, wherein, when the predetermined threshold is updated, the control signal to command the second computing device to perform the action to facilitate correction of the medical anomaly is generated during the second session based on the updated predetermined threshold, and wherein information associated with the updated predetermined threshold is used as feedback in re-training the neural network such that the cognitive model is recursively updated.

14. The non-transitory computer-readable storage medium of claim 13, wherein the first computing device includes a wearable technology device.

15. The non-transitory computer-readable storage medium of claim 13, wherein the comparing of the received medical data to the stored medical data is performed utilizing an analysis operation.

16. The non-transitory computer-readable storage medium of claim 13, wherein the second computing device includes exercise equipment, and wherein the control signal is further configured to change an operational state of the exercise equipment from a first setting to a second setting, the first and second settings being associated with at least one of a speed of the exercise equipment and a resistance of the exercise equipment.

17. The non-transitory computer-readable storage medium of claim 13, wherein the notification further includes an electronic communication sent to a third computing device associated with a second individual.

18. The non-transitory computer-readable storage medium of claim 13, wherein the notification includes at least one of a visual indication and an aural indication rendered by the any capable computing device in the predefined proximity of the individual.

* * * * *